United States Patent
S. et al.

(10) Patent No.: US 9,483,695 B2
(45) Date of Patent: Nov. 1, 2016

(54) COST EFFECTIVE AND ROBUST SYSTEM AND METHOD FOR EYE TRACKING AND DRIVER DROWSINESS IDENTIFICATION

(75) Inventors: Chidanand K. S., West Bengal (IN); Brojeshwar Bhowmick, West Bengal (IN)

(73) Assignee: Tata Consultancy Services Limited, Mumbai, Maharashtra (IN)

(*) Notice: Subject to any disclaimer, the term of this patent is extended or adjusted under 35 U.S.C. 154(b) by 535 days.

(21) Appl. No.: 13/513,495

(22) PCT Filed: Dec. 2, 2010

(86) PCT No.: PCT/IN2010/000781
§ 371 (c)(1),
(2), (4) Date: Jun. 1, 2012

(87) PCT Pub. No.: WO2011/067788
PCT Pub. Date: Jun. 9, 2011

(65) Prior Publication Data
US 2013/0010096 A1  Jan. 10, 2013

(30) Foreign Application Priority Data
Dec. 2, 2009 (IN) .......................... 2784/MUM/2009

(51) Int. Cl.
*G08B 21/06* (2006.01)
*G06K 9/00* (2006.01)
(Continued)

(52) U.S. Cl.
CPC .......... *G06K 9/00604* (2013.01); *A61B 3/113* (2013.01); *A61B 5/18* (2013.01); *G06F 3/013* (2013.01); *G06K 9/0061* (2013.01); *G06K 9/00845* (2013.01); *G08B 21/06* (2013.01)

(58) Field of Classification Search
CPC ......... A61B 3/113; A61B 5/18; G06F 3/013; G06K 9/00604; G06K 9/0061; G08B 21/06
See application file for complete search history.

(56) References Cited

U.S. PATENT DOCUMENTS

| 5,345,281 | A |   | 9/1994 | Taboada et al. |
|-----------|---|---|--------|----------------|
| 5,481,622 | A | * | 1/1996 | Gerhardt ................ A61B 3/113 345/158 |

(Continued)

FOREIGN PATENT DOCUMENTS

EP   1867281 A1   12/2007

OTHER PUBLICATIONS

Oguz, "The Proportion of the Face of Younger Adults Using the Thumb Rule of Leonardo da Vinci," Surgical Radiologic Anatomy, Journal of Clinical Anatomy, 1996, pp. 111-114.*
(Continued)

*Primary Examiner* — Thai Tran
*Assistant Examiner* — Christopher T Braniff
(74) *Attorney, Agent, or Firm* — Merchant & Gould P.C.

(57) ABSTRACT

A cost-effective and robust method for localizing and tracking drowsiness state of the eyes of driver by using images captured by near infrared (IR) camera disposed on the vehicle, the said method comprising the processor implemented steps of: Real-time tracking of the face and localizing eye bounding box within the face bounding box in the captured image by comparing the gray values with threshold using the segmentation process; tracking the eyes by computing the centroid of the eye, target model histogram and target candidate model histogram for one location to another by comparing them to identify distance and calculating the displacement of the target center by the weighted means, wherein the target model histogram and target candidate model histogram are computed based on the feature space; and detecting the drowsiness state of the eyes using histogram equalization, Morphological operations and texture based parameters using histogram and grey level co-occurrence matrices.

8 Claims, 7 Drawing Sheets

(51) Int. Cl.
*A61B 3/113* (2006.01)
*A61B 5/18* (2006.01)
*G06F 3/01* (2006.01)

(56) References Cited

U.S. PATENT DOCUMENTS

| | | | |
|---|---|---|---|
| 5,689,241 A | 11/1997 | Clarke, Sr. et al. | |
| 5,900,819 A | 5/1999 | Kyrtso | |
| 6,283,954 B1 | 9/2001 | Yee | |
| 6,717,518 B1* | 4/2004 | Pirim | B60R 1/04 340/576 |
| 6,927,694 B1 | 8/2005 | Smith et al. | |
| 7,130,446 B2 | 10/2006 | Rui et al. | |
| 7,362,885 B2 | 4/2008 | Hammoud | |
| 8,077,215 B2 | 12/2011 | Nakamura | |
| 2005/0180627 A1* | 8/2005 | Yang et al. | 382/159 |
| 2007/0183662 A1* | 8/2007 | Wang | G06K 9/00248 382/173 |

OTHER PUBLICATIONS

Valckx et al., "Characterization of Echographic Image Texture by Cooccurrence Matrix Parameters," Ultrasound in Med. & Biol., vol. 23, No. 4, 1997, pp. 559-571.*

Tock et al. "Blink Rate Monitoring for a Driver Awareness System" Proceedings of the British Machine Vision Conference. 1992. http://www.bmva.org/bmvc/1992/bmvc-92-054.

Tabrizi P R et al: "Open/ Closed Eye Analysis for Drowsiness Detection" IEEE. 2008. pp. 1-7.

International Search Report for International Application No. PCT/IN2010/000781 mailed Jul. 29, 2011.

* cited by examiner

COST EFFECTIVE AND ROBUST SYSTEM AND METHOD FOR EYE TRACKING AND DRIVER DROWSINESS IDENTIFICATION

This application is a National Stage Application of PCT/IN2010/000781, filed 2 Dec. 2010, which claims benefit of Serial No. 2784/MUM/2009, filed 2 Dec. 2009 in India and which applications are incorporated herein by reference. To the extent appropriate, a claim of priority is made to each of the above disclosed applications.

FIELD OF THE INVENTION

This invention relates to system and method for eye tracking and driver drowsiness identification. More particularly, the invention relates to a cost effective and robust system and method for localizing and tracking drowsiness state of the eyes of a driver for avoiding accidents by using images captured by near infrared (IR) camera disposed on the vehicle

BACKGROUND OF THE INVENTION

Driver fatigue and lack of sleep of drivers especially those that drive large vehicles such as trucks, buses, etc. is a long standing problem. Each year numerous road accidents and fatalities occur as a result of sleepy individuals falling asleep while driving. If at all we can detect the drowsiness state of the driver and have mechanism to warn the driver in such a state, such accidents may be prevented to a large extent.

Absence of a method for detection of driver drowsiness in automobiles is long standing problem.

Some of the inventions which deals with eye tracking and driver drowsiness identification known to us are as follows:

U.S. Pat. No. 6,283,954 to Kingman Yee teaches improved devices, systems, and methods for sensing and tracking the position of an eye make use of the contrast between the sclera and iris to derive eye position. This invention is particularly useful for tracking the position of the eye during laser eye surgery, such as photorefractive keratectomy (PRK), phototherapeutic keratectomy (PTK), laser in situ keratomileusis (LASIK), or the like.

U.S. Pat. No. 5,345,281 to Taboada et al discloses about devices for tracking the gaze of the human eye, and more particularly to an optical device for tracking eye movement by analysis of the reflection off the eye of an infrared (IR) beam.

U.S. Pat. No. 6,927,694 to Smith et al discloses tracking a person's head and facial features with a single on-board camera with a fully automatic system that can initialize automatically, and can reinitialize when needed and provides outputs in realtime. The system as proposed in '694 uses RGB array indexing on the R, G, B components for the pixel that is marked as important, the system also works on different algorithms for daytime and nighttime conditions.

U.S. Pat. No. 5,689,241 to Clarke Sr et al discloses about the device that monitors via the infrared camera the thermal image changes in pixel color of open versus closed eyes of the driver via the temperature sensitive infrared portion of the digitized photographic image passed through a video charge coupling device. The combination of non movement and a decrease in breath temperature, which is a physiological response to hypoventilation thus initiating drowsiness, will trigger the infrared camera to zoom onto the eye region of the driver.

U.S. Pat. No. 5,900,819 to Christos T. Kyrtso discloses about detect drowsiness by measuring vehicle behaviors including speed, lateral position, turning angle.

US20080252745 to Tomokazu Nakamura teaches state-of-eye (including blinking) distinguishing means by calculating a feature value that represents a state of an eye, for an eye-area based on pixel data of pixels that constitute the eye-area. A threshold value setting means calculates a first threshold value representing a feature value at a first transition point from an open state to a closed state and a second threshold value representing a feature value at a second transition point from the closed state to the open state, based on a feature value calculated for a targeted eye when the targeted eye is open.

U.S. Pat. No. 7,362,885 to Riad I. Hammoud teaches that an object tracking method tracks a target object between successively generated infrared video images using a grey-scale hat filter to extract the target object from the background. Where the object is a person's eye, the eye state and decision confidence are determined by analyzing the shape and appearance of the binary blob along with changes in its size and the previous eye state, and applying corresponding parameters to an eye state decision matrix.

U.S. Pat. No. 7,130,446 to Rui et al teaches that automatic detection and tracking of multiple individuals includes receiving a frame of video and/or audio content and identifying a candidate area for a new face region in the frame. One or more hierarchical verification levels are used to verify whether a human face is in the candidate area, and an indication made that the candidate area includes a face if the one or more hierarchical verification levels verify that a human face is in the candidate area. A plurality of audio and/or video cues are used to track each verified face in the video content from frame to frame.

Most of these known drowsiness detection devices rely on sensor technologies. Although some of the approaches have been made using computer vision technology, these drowsiness detection devices use complex methods in order to detect drowsiness and are costlier. Overall these methods aren't adequate and accurate to track eye region to monitor alertness of drivers who suffers from fatigue and lack of sleep.

Thus, in the light of the above mentioned background of the art, it is evident that, there is a need for a system and method for eye tracking and driver drowsiness identification, which is simple, easy to install and provides higher accuracy at a lower cost.

OBJECTIVES OF THE INVENTION

It is a primary objective of the invention to provide a cost effective and robust system and method for localizing and tracking drowsiness state of the eyes of a driver for avoiding accidents by using images captured by near infrared (IR) camera disposed on the vehicle.

It is another objective of the invention to track the eyes independent of pupil effect, wherein morphological erosion is carried out within the face bounding box by performing histogram equalization and Morphology transformation in the eroded image.

It is another objective of the invention to provide a system and method which envisages a robust way of tracking eyes and face using kernel tracking algorithm.

It is another objective of the invention to localize eye portion, in a manner that face is tracked first and then eyes are tracked within the face bounding box with the help of kernel based face and eye tracking algorithms.

It is another objective of the invention to provide a method which collects features such as Morphology transformed image and histogram equalized image subsequently being as parameters for Kernel tracking algorithm.

Yet another objective of the invention is to provide system and method which detect the state of the eyes using histogram equalization, morphological operations and texture based parameters using histogram and grey level co occurrence matrices.

It is another object of the invention to provide the audio or audiovisual to driver to alert the driver after detecting the driver in a drowsiness state.

SUMMARY OF THE INVENTION

Before the method, system, and hardware enablement of the present invention are described, it is to be understood that this invention in not limited to the particular systems, and methodologies described, as there can be multiple possible embodiments of the present invention which are not expressly illustrated in the present disclosure. It is also to be understood that the terminology used in the description is for the purpose of describing the particular versions or embodiments only, and is not intended to limit the scope of the present invention which will be limited only by the appended claims.

The invention provides a cost effective and robust system and method for localizing and tracking drowsiness state of the eyes of a driver for avoiding accidents by using images captured by near infrared (IR) camera disposed on the vehicle.

The present invention embodies a cost effective and robust method for localizing and tracking drowsiness state of the eyes of a driver for avoiding accidents by using images captured by near infrared (IR) camera disposed on the vehicle, the said method comprising the processor implemented steps of: Real-time tracking of the face and localizing eye bounding box within the face bounding box in the captured image by comparing the gray values with threshold using the segmentation process; tracking the eyes by computing the centroid of the eye, computing target model histogram and target candidate model histogram for one location to another location followed by comparing them to identify distance and subsequently calculating the displacement of the target centre by the weighted means, wherein the target model histogram and target candidate model histogram are computed based on the feature space which includes histogram equalized image range and Morphology transformed image; and detecting the drowsiness state of the eyes using histogram equalization, Morphological operations and texture based parameters using histogram and grey level co-occurrence matrices.

In yet another aspect of the invention an alert means is provided for warning the driver using detected drowsiness state of the eyes for avoiding collision, wherein the alert means can be audio and audio visual device including but not limited to an alarm, a voice based caution, an Indicator with display. In accordance with another aspect of the invention, near IR camera is disposed inside of the vehicle facing towards from the driver.

BRIEF DESCRIPTION OF DRAWINGS

The foregoing summary, as well as the following detailed description of preferred embodiments, is better understood when read in conjunction with the appended drawings. For the purpose of illustrating the invention, there is shown in the drawings example constructions of the invention; however, the invention is not limited to the specific methods and apparatus disclosed in the drawings.

DETAILED DESCRIPTION OF THE INVENTION

Some embodiments of this invention, illustrating its features, will now be discussed in detail. The words "comprising," "having," "containing," and "including," and other forms thereof, are intended to be equivalent in meaning and be open ended in that an item or items following any one of these words is not meant to be an exhaustive listing of such item or items, or meant to be limited to only the listed item or items. It must also be noted that as used herein and in the appended claims, the singular forms "a," "an," and "the" include plural references unless the context clearly dictates otherwise. Although any systems and methods similar or equivalent to those described herein can be used in the practice or testing of embodiments of the present invention, the preferred, systems and methods are now described. The disclosed embodiments are merely exemplary of the invention, which may be embodied in various forms by a person skilled in the art.

A cost effective and robust method for localizing and tracking drowsiness state of the eyes of a driver for avoiding accidents by using images captured by near infrared (IR) camera disposed on the vehicle, the said method comprising the processor implemented steps of:
a) Real-time tracking of the face and localizing eye bounding box within the face bounding box in the captured image by comparing the gray values with threshold using the segmentation process;
b) tracking the eyes by computing the centroid of the eye, target model histogram and target candidate model histogram for one location to another location followed by comparing them to identify distance and subsequently calculating the displacement of the target centre by the weighted means, wherein the target model histogram and target candidate model histogram are computed based on the feature space which includes histogram equalized image range and Morphology transformed image; and
c) detecting the drowsiness state of the eyes using histogram equalization, Morphological operations and texture based parameters using histogram and grey level co-occurrence matrices.

According to one exemplary embodiment of the invention, a cost effective and robust system comprises of a near IR camera disposed on the vehicle facing towards the driver for capturing an image; and a processor is housed therein for analyzing the captured image in real-time for localizing and tracking drowsiness state of the eyes of the driver for avoiding accidents.

Figure 1:
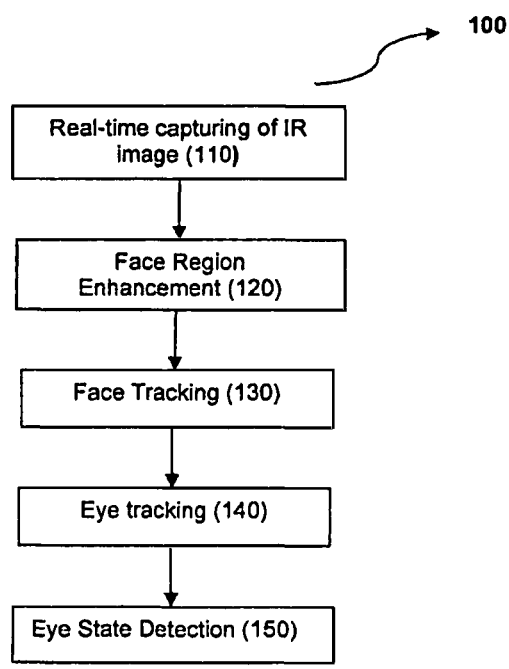
FIG. 1 is flowchart which illustrates a method for localizing and tracking drowsiness state of the eyes of a driver for accidents according to various embodiments of the invention.

FIG. 1 is flowchart which illustrates a method 100 for localizing and tracking drowsiness state of the eyes of a driver for preventing accidents according to various embodiments of the invention.

In one exemplary embodiment of the invention, a cost effective method for localizing and tracking drowsiness state of the eyes of a driver for avoiding accidents by using images 110 captured by near infrared (IR) camera disposed on the vehicle. In accordance with another aspect of the invention, near IR camera can be disposed either outside or inside of the vehicle facing towards from the driver. In one example embodiment of the invention, the near IR camera is disposed inside of the vehicle facing towards from the driver.

In accordance with one aspect of the invention the resolution of the near IR camera is 352*288. In accordance with one aspect of the invention the IR range of the near IR camera can be selected from a range of (0.7-1) to 5 Microns for detecting and tracking the pedestrians. In accordance with one aspect of the invention the temperature range of the near IR camera can be selected from 740 to 3,000-5,200 Kelvin for detecting and tracking the pedestrians.

In accordance with one aspect of the invention the processor can be disposed either in the body of the near IR camera, outside or inside, top or on the dashboard of the vehicle. In one exemplary embodiment of the invention, the processor is disposed in the body of the near IR camera. In accordance with another aspect of the invention the processor can be selected from the group of Davinci DM6446 Processor, ADSP-BF533, 750 MHz Blackfin Processor.

The above said cost effective method comprises various processor implemented steps. Tracking small objects such as eyes in an entire image is difficult. Hence to localize the search of eyes, in the first step of the proposed method, the face is tracked first and then eyes are tracked, with in the face bounding box.

The processor executes the code that identifies 120 the shape of the eyes and facial landmarks such as eyebrow, nose tip and vertical face centre using the segmentation process. In order to track the face, the processor executes the code that determines face coordinates using the following equation:

Face_width=face_extreme_right−face_extreme_left

Face_height=2*(nose_tip_position−eye_brow_position)−eye_brow_position

In order to track the eyes, the processor executes the code that determines bounding box of eyes using segmentation process. In order to track the face 130, the processor executes the code that collects the features which is just the grey values greater than the threshold obtained from segmentation process. In order to track the eyes 140, the processor executes the code that collects feature which is histogram equalization in the bounding box of face and Morphology transformation in the bounding box of the face.

The main obstacle in tracking eyes is to get rid of pupil effect. In order to make eye tracking independent of pupil effect, first morphological erosion is carried out with in the face bounding box by the processor. From this eroded image, histogram equalization and Morphology transformation are done.

The Histogram equalization produces an output image that has a uniform histogram by spreading the levels of an input image over wide range of intensity scale. After the processor executes the code that applies Histogram equalization on the output image, the dark image becomes much darker and bright image much brighter. The processor executes the code that extracts dark objects (i.e. eyes) from bright background (i.e. face bounding box) using Morphology transformation.

In the second step of the proposed method, the processor tracks the eyes by computing the centroid of the eye, and calculating the target model histogram and target candidate model histogram for one location to another location by comparing them to identify distance and subsequently calculating the displacement of the target centre by the weighted means, wherein the target model histogram and target candidate model histogram are computed based on the feature space which includes histogram equalized image range and Morphology transformed image.

For eye tracking 140, the processor executes the following steps: In the first step, the processor executes the code that considers the centroid of eye blob as centre m0, and then it calculates the target model histogram by considering the feature space.

if (hist_eq($i,j$)<max_range & &hist_eq($i,j$)>min_range)

Compute 32 bin histogram $\hat{q}$ on Morphological transformed image.

Target model: $\hat{q}=\{\hat{q}_n\}$ $u$=1,2,3, ... 32, $\Sigma\hat{q}_n$=1

From next frame onwards, centre of the target is initialized at its previous location (y0) and the processor executes the code that calculates target candidate histogram by considering the same feature space.

if (hist_eq($i,j$)<max_range & &hist_eq($i,j$)>min_range)

Update 32 bin histogram $\hat{p}$ on Morphological transformed image.

Now, the processor executes the code that calculates the distance between target model and target candidate histogram, $d(y) = \sqrt{1 - \rho[p(y), \hat{q}]}$, where $\rho[\bullet]$ is the bhattacharya coefficient between p and q.

Now, the processor executes the code that calculates the displacement of the target centre by the weighted mean.

$$\hat{y}_1 = \frac{\sum_{i=1}^{n_h} x_i \omega_i}{\sum_{i=1}^{n_h} \omega_i} \text{ where,}$$

$$\omega_i = \sum_{u=1}^{\omega} \sqrt{\frac{\hat{q}_u}{\hat{p}_u(\hat{y}_0)}},$$

Once the new location of target is found, the processor executes the code that
1) Computes target candidate histogram at new location with the same feature space involving histogram equalized image range and Morphology transformed image.
2) Then Computes $\rho[\hat{p}(y_1), \hat{q}]$
3) While $\rho[\hat{p}(y_1), \hat{q}] < \rho[\hat{p}(y_0), \hat{q}]$
   do $y_1 \leftarrow (y_0 + y_n)/2$
   evaluate $\rho[\hat{p}(y_1), \hat{q}]$
4) If $\|y_1 - y_0\| < \epsilon$, stop
   Otherwise sets $y_0 \leftarrow y_1$ and derive weights, then new location and goto step 1

With the above tracking process, there would be drifting of eyes which is mainly because:
a) In morphological transformed image, noise also appears brighter and it leads to ambiguity whether the pixel is nose pixel or an eye pixel.
b) Position and velocity information is not included.

In order to solve these problems, the processor maps the eye to eyebrow in the morphology transformed image to identify the eye pixel thereby avoiding the nose pixel which appears brighter in such image.

In order to map the eye to eyebrow in the morphology transformed image, the processor executes the following steps:

a) Eye to eyebrow mapping
Since eye and eyebrow appears one below the other, we use this clue to discriminate whether the pixel is an eye pixel or a nose pixel.

Eye to eyebrow mapping in Morphology transformed image involves

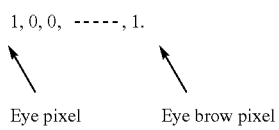

Whereas nose to eyebrow mapping in Morphology transformed image involves either.

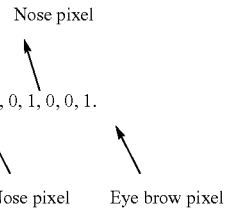

b) Direction estimation
In the first 4 frames, centroid of eye position is stored in a FIFO (First-in First-out) or queue. For the current frame, before calculating the new centroid using kernel tracking algorithm, the processor executes the code that updates centroids using to the equation mentioned below.

$cr$=previous_$cr$+(fifo$cr$[3]−fifo.$cr$[0])/4;

$cc$=previous.$cc$+(fifo.$cc$[3]−fifo.$cc$[0])/4

If there is a sudden jerk which occurs naturally in the car environment, the head position and eye position changes drastically. In order to track the eyes, the processor executes the codes that detects the change in head position in the current frame with respect to previous frame, wherein the condition is ‖curr_diff−prev_diff‖>‖velocity‖ curr_diff=‖track[0].$cr$−fifo1.$cr$(2))‖+‖track[0].$cc$−fifo1.$cc$[2]‖ prev_diff=‖fifo1.$cr$[1]−fifo1.$cr$[2]‖+‖fifo1.$cc$[1]−fifo1.$cc$[2]‖ velocity=‖fifo1.$cr$[3]−fifo1.$cr$[0]‖+‖fifo1.$cc$[3]−fifo1.$cc$[0]‖/4

Once this condition is checked and if the condition is set then the Kernel tracking algorithm fails to track the eyes, but it still tracks the face since the face is bigger in size compared to eyes.

In order to still track the eyes even when there is a large change (jerks), template matching of eyes based on SAD (Sum of absolute differences) is calculated by the processor. At the end of Kernel tracking algorithm, the tracked eyes are stored as template images.

In the tracking process, the boundary box of eyes is located. In the final step, the processor detects the drowiness state of the eyes 150 using histogram equalization, Morphological operations and texture based parameters using histogram and grey level co-occurrence matrices.

Such processor implemented methods will now be discussed in detail:

Before going to histogram equalization process, the processor executes the codes that extend the boundary box of the eyes upwards up to centroid of eyebrows. In this region, the processor executes the code that applies a histogram equalization process on the bounding box of the eyes, wherein the histogram equalization is a method in image processing of contrast adjustment using the image's histogram. Histogram equalization is the technique by which the dynamic range of the histogram of an image is increased. Histogram equalization assigns the intensity values of pixels in the input image such that the output image contains a uniform distribution of intensities. It improves contrast and the goal of histogram equalization is to obtain a uniform histogram. This technique can be used on a whole image or just on a part of an image.

Histogram equalization redistributes intensity distributions. If the histogram of any image has many peaks and valleys, it will still have peaks and valley after equalization, but peaks and valley will be shifted. Because of this, "spreading" is a better term than "flattening" to describe histogram equalization. In histogram equalization, each pixel is assigned a new intensity value based on its previous intensity level.

In the next step, the processor eliminates the brighter pupil effect of the histogram equalized image by computing the line erosion of such image with a structuring element, wherein the width of the structuring element is equal to ⅓ of eye brow width and height of the structuring element is equal to one.

In order to eliminate the brighter pupil effect, the processor executes the following steps:

Consider a discrete grey scale image {x} and let $n_i$ be the number of occurrences of grey level i. The probability of an occurrence of a pixel of level i in the image is $$p_x(i)=p(x=i)=n_i/n, \ 0 \leq i \leq L$$

L being the total number of grey levels in the image, n being the total number of pixels in the image, and $p_x$ being in fact the image's histogram, normalized to [0,1].

defines the cumulative distribution function corresponding to $p_x$ as $$cdf_x(i) = \sum_{j=0}^{i} p_x(j).$$

which is also the image's accumulated normalized histogram.

Further a transformation is created of the form y=T(x) to produce a new image {y}, such that its CDF will be linearized across the value range, i.e.

$$cdf_x(i)=iK. \text{ for some constant } K.$$

The properties of the CDF allow us to perform such a transform $$y=T(x)=cdf_x(x).$$

Notice that the T maps the levels into the range [0, 1]. In order to map the values back into their original range, the following simple transformation needs to be applied on the result:

$$y'=y.(\max\{x\}-\min\{x\})+\min\{x\}.$$

After Histogram equalization, the dark portions in grey level image appears more darker and bright portions in grey level image appears brighter. Since bright pupil effect in eye appears much brighter or sometimes no bright pupil effect is detected, In order to suppress bright pupil effect, line erosion is done with a structuring element width=⅓ rd of eye brow width and structuring element height equal to one.

If A is the grey level image and B is the structuring element, for sets A and B in $Z^2$, the erosion of A by B, $$A \ominus B=\{z \epsilon E | B_z \subseteq A\}$$

After erosion, small unwanted component would be there. In order to suppress unwanted components and to retain eye region, grey scale opening will be done with a structuring element height and structuring element width equal to 3.

In mathematical morphology, opening is the dilation of the erosion of a set A by a structuring element B:

If A is the grey level image and B is the structuring element, for sets A and B in $Z^2$, the morphological opening of A by B, $$A \circ B=(A \ominus B) \oplus B,$$

In the next step, the processor uses histogram based approach to texture analysis which is based on the intensity value concentrations on all or part of an image represented as a histogram to identify the state of the eye, wherein the value of Uniformity or Angular secondary moment (ASM) texture parameter occurs high for closed eye and low for open eye.

In order to do the texture analysis, the processor executes the following steps:

In the first step, the processor executes the codes that implements the texture Based Analysis on the image.

Texture is a property that represents the surface and structure of an Image. Texture can be defined as a regular repetition of an element or pattern on a surface. Image textures are complex visual patterns composed of entities or regions with sub-patterns with the characteristics of brightness, color, shape, size, etc. An image region has a constant texture if a set of its characteristics are constant, slowly changing or approximately periodic. Texture analysis is a major step in texture classification, image segmentation and image shape identification tasks. Image segmentation and shape identification are usually the preprocessing steps for target or object recognition in an image.

Mathematical procedures to characterize texture fall into two major categories,

1. Statistical and
2. Syntactic

Statistical approaches compute different properties and are suitable if texture primitive sizes are comparable with the pixel sizes. These include Fourier transforms, convolution filters, co-occurrence matrix, spatial autocorrelation, fractals, etc.

Syntactic and hybrid (Combination of statistical and syntactic) methods are suitable for textures where primitives can be described using a larger variety of properties than just tonal properties; for example shape description. Using these properties, the primitives can be identified, defined and assigned a label. For grey-level images, tone can be replaced with brightness.

One of the simplest approaches for describing texture is to use statistical moments of the grey level histogram of an image or region. Histogram based approach to texture analysis is based on the intensity value concentrations on all or part of an image represented as a histogram. Common features include moments such as mean, variance, dispersion, mean square value or average energy, entropy, skewness and kurtosis.

Let Z be a random variable denoting grey levels and let $\rho(Z_i)$, I=0, 1, 2, L-1 be the corresponding histogram, where L is the number of distinct grey levels.

The nth moment of Z about the mean is $$\mu_n(Z) = \sum_{i=0}^{L-1} (Z_i - m)^n \rho(Z_i),$$

where m is the mean value of Z (the average grey level)

$$m = \sum_{i=0}^{L-1} Z_i \rho(Z_i).$$

In one embodiment of the present invention, we used "Uniformity or Angular secondary moment (ASM)" texture parameter. This is a measure of local homogeneity. High values of ASM occur when the pixels in the moving window are very similar.

This uniformity is given by the equation below.

$$U = \sum_{i=0}^{L-1} p^2(Z_i).$$

The value of uniformity lies between 0 to 1. This parameter is high for closed eye and low for open eye.

Optionally the processor uses contrast of the grey level co-occurrence matrix to identify the state of the eyes by detecting the band of N frames is having the same property then the eye is closed.

In order to detect the eye state, the processor executes the following steps: A co-occurrence matrix, also referred to as a co-occurrence distribution, is defined over an image to be the distribution of co-occurring values at a given offset. Mathematically, a co-occurrence matrix C is defined over an n×m image I, parameterized by an offset (Δx,Δy), as:

$$C(i, j) = \sum_{p=1}^{n} \sum_{q=1}^{m} \begin{cases} 1, & \text{if } I(p, q) = i \text{ and } I(p + \Delta x, q + \Delta y) = j \\ 0, & \text{otherwise} \end{cases}$$

In this grey level co-occurrence matrix, "Contrast" we have found one parameter "Contrast" which is distinguishing factor for detecting eye state.
the processor executes the codes that calculates the contrast by using the following equation.

$$\text{Contrast} = \sum_{i,j} (i - j)^2 p(i, j).$$

For classification, the processor is used to observe first T frames from where the tracking starts. For every frame, the processor executes the codes that calculates μ and σ dynamically for every feature, with initialization μ=feature value, σ=0. The frame where feature>μ+3*σ or feature<μ−3*σ the updation of these two parameters are freezed. Once a band of N frames are found having the same property the closed eye is signaled.

Figure 2A:
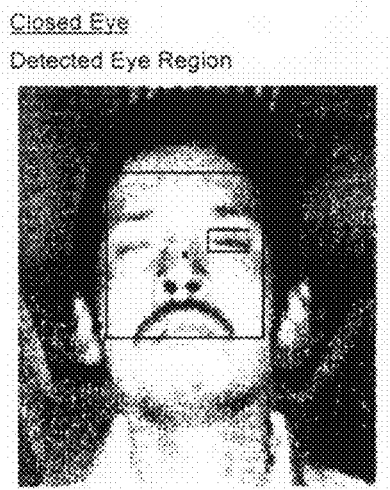
FIG. 2A illustrates the detected eye region for the closed eye in one exemplary head position of the driver in accordance with the invention.

FIG. 2A illustrates the detected eye region for the closed eye in one exemplary head position of the driver in accordance with the invention.

Figure 2B:
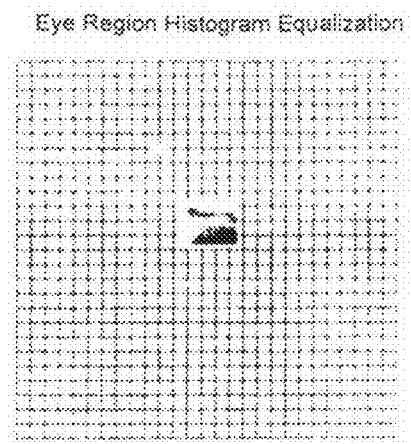
FIG. 2B illustrates the histogram equalization of the detected eye region for the closed eye in one exemplary head position of the driver in accordance with the invention.

FIG. 2B illustrates the histogram equalization of the detected eye region for the closed eye in one exemplary head position of the driver in accordance with the invention.

Figure 2C:
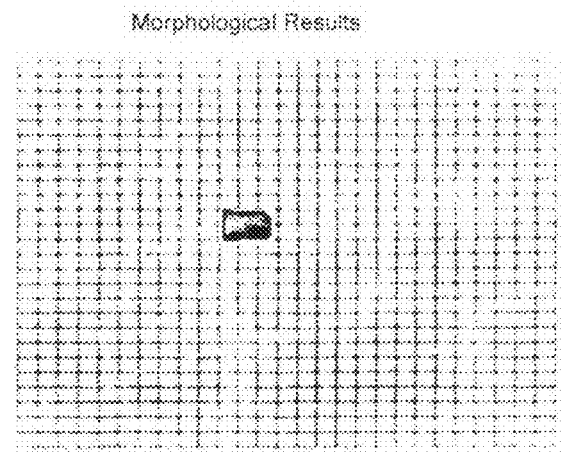
FIG. 2C illustrates morphological results of the histogram equalization of the detected eye region for the closed eye in one exemplary head position of the driver in accordance with the invention.

FIG. 2C illustrates morphological results of the histogram equalization of the detected eye region for the closed eye in one exemplary head position of the driver in accordance with the invention.

Figure 2D:
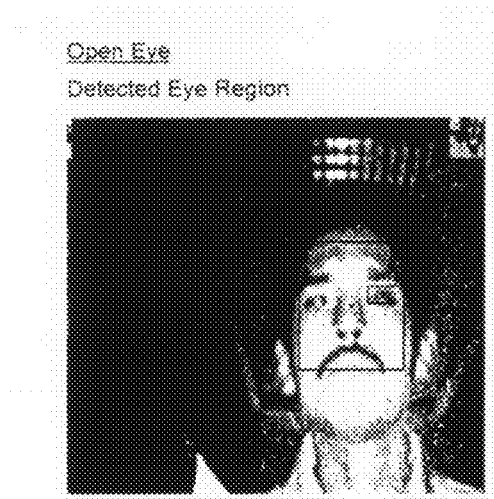
FIG. 2D illustrates the detected eye region for open eye in one exemplary head position of the driver in accordance with the invention.

FIG. 2D illustrates the detected eye region for open eye in one exemplary head position of the driver in accordance with the invention.

Figure 2E:
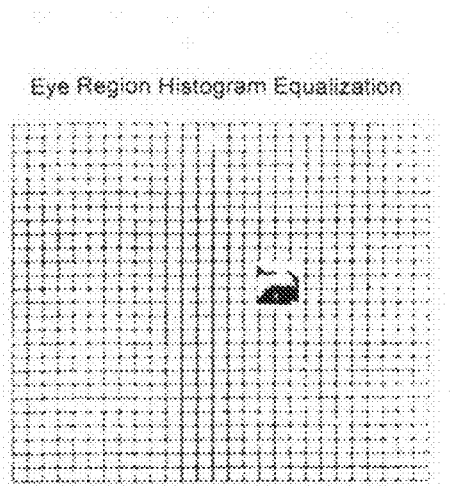
FIG. 2E illustrates the histogram equalization of the detected eye region for open eye in one exemplary head position of the driver in accordance with the invention.

FIG. 2E illustrates the histogram equalization of the detected eye region for open eye in one exemplary head position of the driver in accordance with the invention.

Figure 2F:
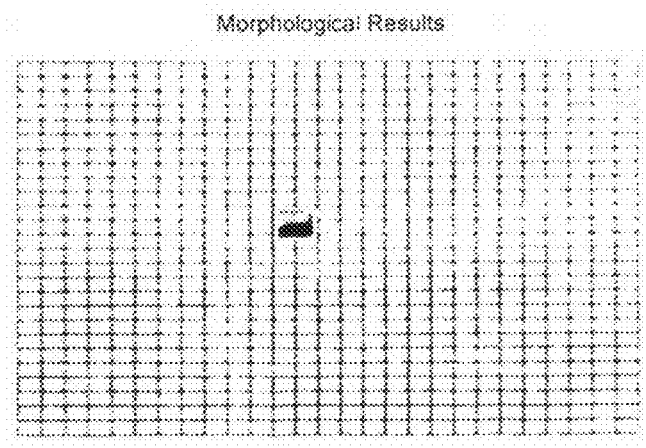
FIG. 2F illustrates morphological results of the histogram equalization of the detected eye region for open eye in one exemplary head position of the driver in accordance with the invention.

FIG. 2F illustrates morphological results of the histogram equalization of the detected eye region for open eye in one exemplary head position of the driver in accordance with the invention.

Figure 3A:
FIG. 3A illustrates the detected eye region for the closed eye in another exemplary head position of the driver in accordance with the invention.

FIG. 3A illustrates the detected eye region for the closed eye in another exemplary head position of the driver in accordance with the invention.

Figure 3B:
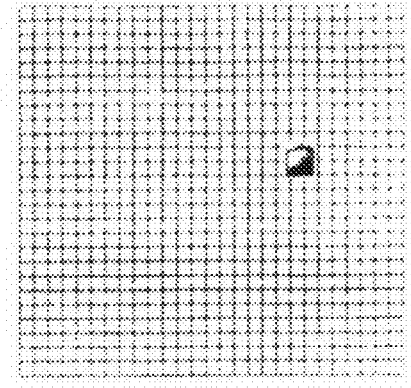
FIG. 3B illustrates the histogram equalization of the detected eye region for the closed eye in another exemplary head position of the driver in accordance with the invention.

FIG. 3B illustrates the histogram equalization of the detected eye region for the closed eye in another exemplary head position of the driver in accordance with the invention.

Figure 3C:
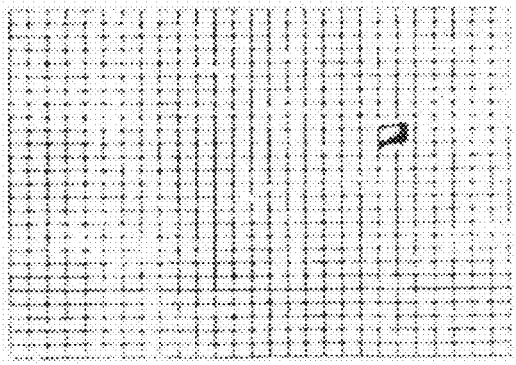
FIG. 3C illustrates morphological results of the histogram equalization of the detected eye region for the closed eye in another exemplary head position of the driver in accordance with the invention.

FIG. 3C illustrates morphological results of the histogram equalization of the detected eye region for the closed eye in another exemplary head position of the driver in accordance with the invention.

Figure 3D:
FIG. 3D illustrates the detected eye region for open eye in another exemplary head position of the driver in accordance with the invention.

FIG. 3D illustrates the detected eye region for open eye in another exemplary head position of the driver in accordance with the invention.

Figure 3E:
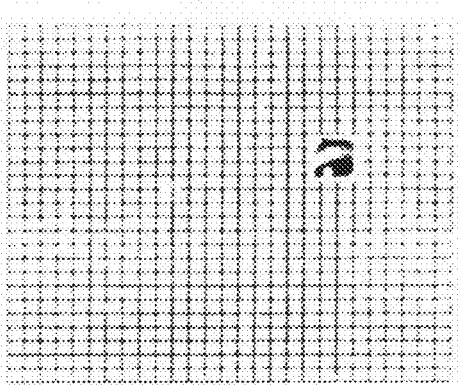
FIG. 3E illustrates the histogram equalization of the detected eye region for open eye in another exemplary head position of the driver in accordance with the invention.

FIG. 3E illustrates the histogram equalization of the detected eye region for open eye in another exemplary head position of the driver in accordance with the invention.

Figure 3F:
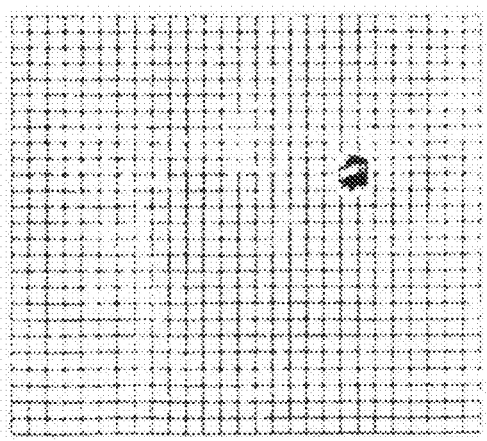
FIG. 3F illustrates morphological results of the histogram equalization of the detected eye region for open eye in another exemplary head position of the driver in accordance with the invention.

FIG. 3F illustrates morphological results of the histogram equalization of the detected eye region for open eye in another exemplary head position of the driver in accordance with the invention.

Figure 4A:
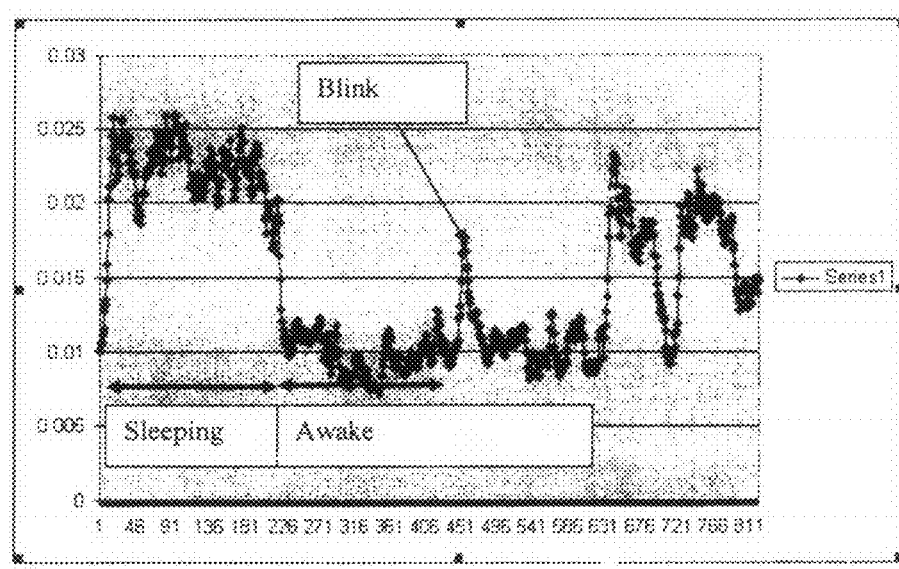
FIGS. 4A & 4B shows the graphs which illustrates driver drowsiness identification statues according to the exemplary embodiments of the invention.
Figure 4B:
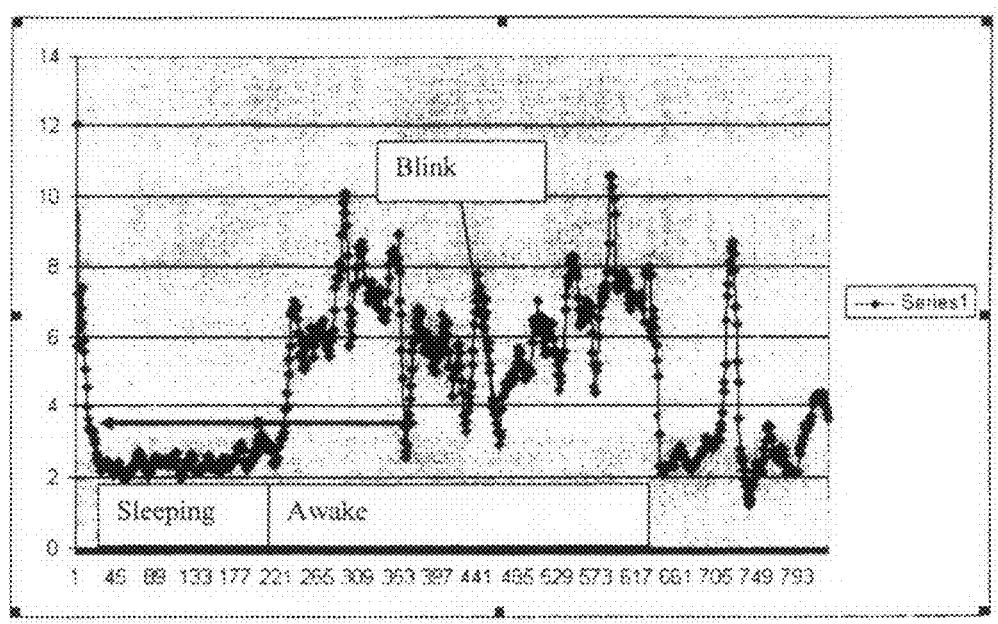

FIGS. 4A & 4B shows the graphs which illustrates driver drowsiness identification statues according to the exemplary embodiments of the invention.

In yet another aspect of the invention the provision for warning the driver using detected drowsiness state of the eyes for avoiding collision using an alert means, wherein the alert means can be audio and audio visual devices, sounding an alarm, a voice based caution, an Indicator and display.

The preceding description has been presented with reference to various embodiments of the invention. Persons skilled in the art and technology to which this invention pertains will appreciate that alterations and changes in the described process and methods of operation can be practiced without meaningfully departing from the principle, spirit and scope of this invention.

ADVANTAGES OF THE INVENTION

Thus some of the advantages of the system and a Method proposed in the invention for Eye Tracking and Driver Drowsiness Identification are:

1. More accuracy in terms of tracking the position of the eye using histogram equalization, morphological operations and texture based analysis.
2. Adaptation of the system with respect to change in the position of eye in case of sudden jerks.
3. Driver Warning strategies coupled to drowsiness detection application in the system.
4. Track the eyes independent of pupil effect, morphological erosion is carried out within the face bounding box by performing histogram equalization and Morphology transformation in the eroded image.

We claim:

1. A computer implemented method for determining in real time a drowsiness state of a driver while driving by using images captured by a near infrared (IR) camera disposed on a vehicle, the method comprising:
    determining a face bounding box by determining face coordinates using a segmentation process by collecting one or more features of a face and by determining a face height based on a difference between at least one of a nose tip position, an eye brow position, and co-ordinates of the eye brow position;

real time tracking of the face by collecting grey values of features of the face greater than threshold values of said features, obtained from the segmentation process;

tracking the eyes by computing a centroid of the eye, and calculating a target model histogram and a target candidate model histogram based on a range of intensity of a histogram equalized image and a morphology transformed image;

real time tracking of the eyes within a face bounding box and collecting a histogram equalization and a morphology transformation in the face bounding box;

calculating the distance between the target model histogram and the target candidate model histogram and calculating a displacement of the target centre; and detecting a drowsiness state of a driver from the eyes by using at least one of histogram equalization, morphological operations and texture based parameters by using histogram and grey level co-occurrence matrices.

2. The method of claim 1, wherein performing the histogram equalization and the morphological operation results in a contrast enhancement of the face bounding box.

3. The method of claim 1, further comprising generating an alert for warning the driver based on the drowsiness state of the driver.

4. The method of claim 1, wherein the near IR camera is disposed outside or inside the vehicle, and wherein the near IR camera faces towards the driver.

5. The method of claim 1, wherein the tracking of the eyes in real time further comprise detecting a change in head position in a current frame with respect to a previous frame, wherein the change in the head position is detected using the Kernel tracking algorithm.

6. The method of claim 1, wherein detecting the drowsiness state of the driver further comprises:

extending a bounding box of the eyes upwards to a centroid of the eyebrows;

applying the histogram equalization on the bounding box of the eyes;

eliminating a brighter pupil effect of a histogram equalized image by computing a line erosion of the histogram equalized image with a structuring element, wherein a width of the structuring element is equal to ⅓ of eyebrow width and a height of the structuring element is equal to one; and using a histogram based approach to texture analysis which is based on the intensity value concentrations on all or part of an image represented as a histogram to identify the state of the eye, wherein the value of uniformity or Angular secondary moment (ASM) texture parameter occurs high for closed eye and low for open eye.

7. A system for determining drowsiness state of a driver for avoiding accidents by using images captured by a near infrared (IR) camera disposed on a vehicle, the system comprises:

a processor; and a memory coupled to the processor, wherein the processor is capable of executing programmed instructions stored in the memory to:

determine a face bounding box by determining face coordinates using a segmentation process by collecting one or more features of a face and determine a face height based on a difference between at least one of a nose tip position, an eye brow position, and co-ordinates of the eye brow position;

track the face real time by collecting grey values of features of the face greater than threshold values of said features, obtained from the segmentation process;

track the eyes by computing a centroid of the eye, and calculating a target model histogram and a target candidate model histogram based on a range of intensity of a histogram equalized image and a morphology transformed image, wherein the eyes are tracked real time within a face bounding box and a histogram equalization and a morphology transformation in the face bounding box are collected;

calculate the distance between the target model histogram and the target candidate model histogram and calculating a displacement of the target centre; and detect a drowsiness state of a driver from the eyes by using at least one of histogram equalization, morphological operations and texture based parameters by using histogram and grey level co-occurrence matrices.

8. The system of claim 7, wherein the processor is further configured to generate an alert for warning the driver based on the drowsiness state of the driver.

* * * * *